US008554353B2

(12) United States Patent
Jeong et al.

(10) Patent No.: US 8,554,353 B2
(45) Date of Patent: Oct. 8, 2013

(54) FABRICATION SYSTEM OF CIGS THIN FILM SOLAR CELL EQUIPPED WITH REAL-TIME ANALYSIS FACILITIES FOR PROFILING THE ELEMENTAL COMPONENTS OF CIGS THIN FILM USING LASER-INDUCED BREAKDOWN SPECTROSCOPY

(75) Inventors: Sungho Jeong, Gwangju (KR); Seokhee Lee, Gwangju (KR); Hee-Sang Shim, Gwangju (KR)

(73) Assignee: Gwangju Institute of Science and Technology, Buk-Gu, Gwangju (KR)

( * ) Notice: Subject to any disclaimer, the term of this patent is extended or adjusted under 35 U.S.C. 154(b) by 0 days.

(21) Appl. No.: 13/326,247

(22) Filed: Dec. 14, 2011

(65) Prior Publication Data

US 2013/0158698 A1    Jun. 20, 2013

(51) Int. Cl.
*G06F 19/00* (2011.01)

(52) U.S. Cl.
USPC ............ 700/121; 700/103; 700/104; 700/123

(58) Field of Classification Search
USPC .................... 700/113; 198/341.08, 341.09
See application file for complete search history.

(56) References Cited

U.S. PATENT DOCUMENTS

| | | | |
|---|---|---|---|
| 5,207,309 A * | 5/1993 | Simpkin et al. ........... 198/341.09 |
| 6,107,600 A * | 8/2000 | Kurosawa ................... 219/121.8 |
| 6,990,386 B2 * | 1/2006 | Tanaka et al. ................. 700/113 |
| 7,050,878 B2 * | 5/2006 | Yamazaki et al. ............. 700/121 |
| 7,078,246 B2 * | 7/2006 | Yamaguchi et al. .............. 438/7 |
| 7,079,975 B1 * | 7/2006 | Halliyal et al. ................ 702/172 |
| 7,695,985 B2 * | 4/2010 | Tanaka et al. ...................... 438/7 |
| 7,820,531 B2 * | 10/2010 | Matsunobu et al. .......... 438/487 |
| 7,821,627 B2 * | 10/2010 | Li ............................... 356/237.2 |
| 7,842,520 B2 * | 11/2010 | Maruyama et al. ............. 438/16 |
| 2005/0174584 A1 * | 8/2005 | Chalmers et al. ............. 356/630 |
| 2006/0155413 A1 * | 7/2006 | Yamazaki et al. ............. 700/121 |
| 2008/0094081 A1 * | 4/2008 | Nguyen et al. ................ 324/750 |
| 2009/0162970 A1 * | 6/2009 | Yang .............................. 438/96 |
| 2010/0006785 A1 * | 1/2010 | Finarov ..................... 250/559.05 |
| 2010/0059693 A1 * | 3/2010 | Svidenko et al. .......... 250/492.3 |
| 2010/0087016 A1 * | 4/2010 | Britt et al. ......................... 438/7 |
| 2010/0167431 A1 * | 7/2010 | Yamaguchi et al. ............ 438/16 |
| 2010/0330711 A1 * | 12/2010 | Schlezinger ...................... 438/7 |
| 2011/0033957 A1 * | 2/2011 | Holden et al. .................. 438/16 |
| 2011/0244603 A1 * | 10/2011 | Dovrat ............................... 438/7 |
| 2011/0276166 A1 * | 11/2011 | Atanasoff ...................... 700/104 |
| 2012/0160633 A1 * | 6/2012 | Jiang et al. ............... 198/341.09 |

* cited by examiner

*Primary Examiner* — Kavita Padmanabhan
*Assistant Examiner* — Christopher E Everett
(74) *Attorney, Agent, or Firm* — Nath, Goldberg & Meyer; Joshua B. Goldberg; Megan B. Doughty

(57) ABSTRACT

A fabrication processing system is used to produce copper indium gallium selenide ($CuIn_{1-x}Ga_xSe_2$ or CIGS) thin film solar cells, more particularly to a fabrication processing system CIGS of thin film solar cells, equipped with real-time analysis facilities for profiling the elemental components of CIGS thin film using laser-induced breakdown spectroscopy. The system provides a process control system for determining whether abnormalities are present or not by measuring a physical and chemical properties on a continuous production process lines of CIGS thin film solar cell in real time, and performs a production and quality management at the same time by providing a feedback to CIGS fabrication process.

13 Claims, 14 Drawing Sheets

Fig. 2

| | SIMS | AES | SEM/EDS | XRF | GD-MS | IBS |
|---|---|---|---|---|---|---|
| Depth profiling resolution | 1-20 nm | 10-100 Å | 0.5-3 micron | >1 micron | 100 to 300 nm | 30 to 100 nm |
| Lateral resolution | >10 micron | 0.01-2 micron | 0.2 to 2 micron | 10's micron to 1 mm | >1000 micron | 10 micron |
| Measurement time for 2 micron film | hours | hours | minutes | minutes | 10's minutes to hr | seconds |
| Detection limit | ppb | 1000 to 10000 ppm | 1000 to 10000 ppm | 100 to 1000 ppm | Sub-ppm | ppm |
| Sample preparation | Minor sectioning to put into the sample holder | Little sample prep but the sample needs to be conductive | Coating with Ir or Au | Minor palletizing or little prep | Minor surfacing cleaning or little sample prep; mainly conductive sample | Little sample prep |
| Measurement environment | High vacuum | High vacuum | High vacuum | in air | High vacuum | in air/ in chamber with buffer gas |
| Elemental coverage | Most of elements in the periodic table | Most of elements in the periodic table (except H & he) | Difficult for elements lighter than Carbon | Difficult for light elements like Na, O, N, C, B, Be, Li etc. | Most of elements in the periodic table | Most of elements in the periodic table |
| Instrument cost | 500K to 1 Mil USD | 350 to 500K USD | 500 to 750K USD (with SEM) | 80 to 150K USD | 400 to 500K USD | 120 to 170K USD |

▭ Depth profiling for thin film structure difficult
▭ Requires high vacuum and expensive instrument cost

Fig. 10A     Fig. 10B
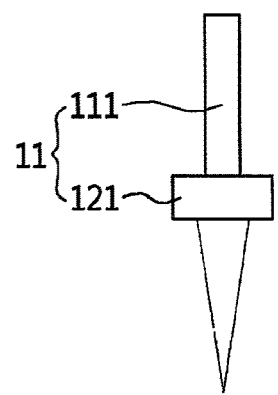 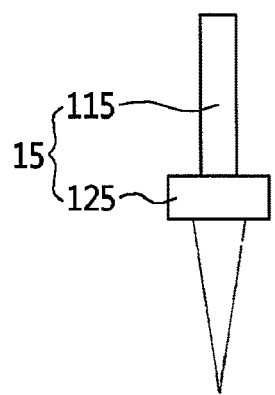

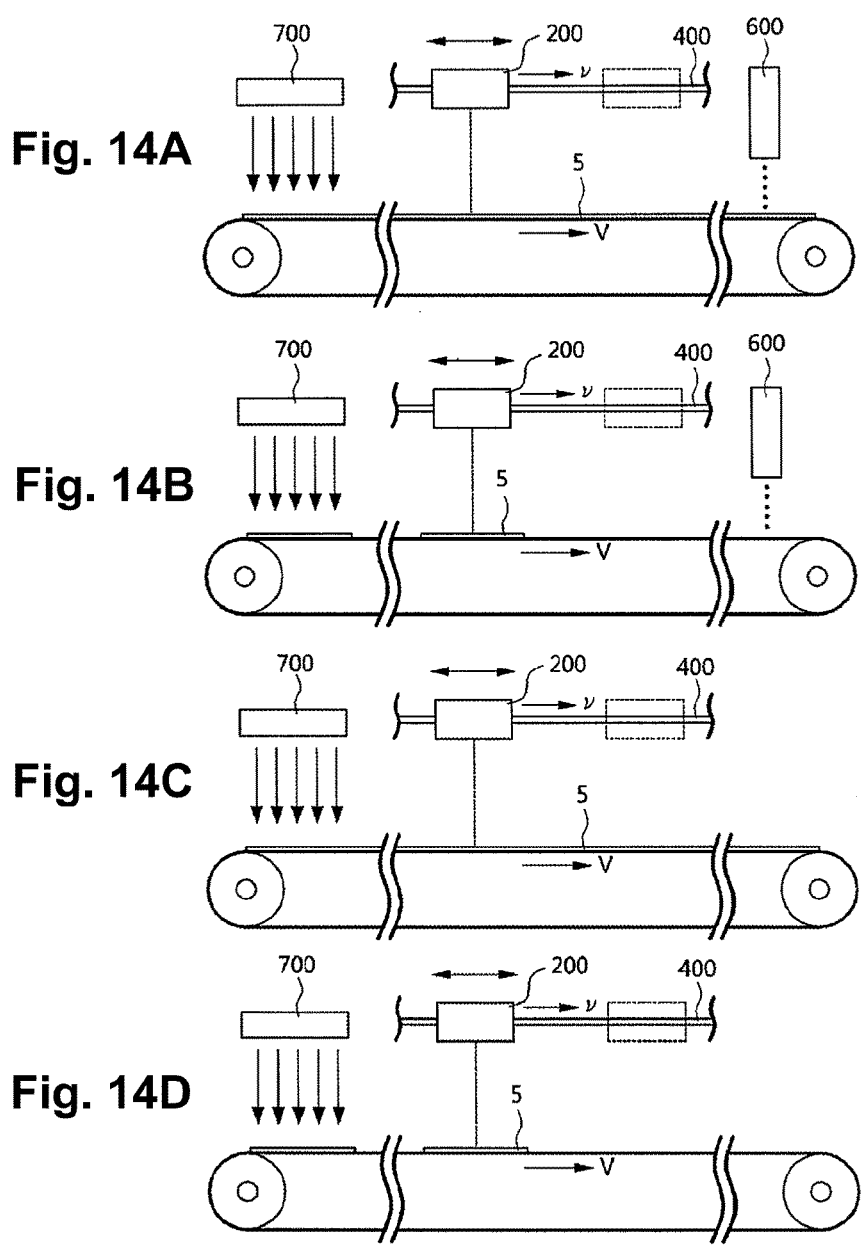

FABRICATION SYSTEM OF CIGS THIN FILM SOLAR CELL EQUIPPED WITH REAL-TIME ANALYSIS FACILITIES FOR PROFILING THE ELEMENTAL COMPONENTS OF CIGS THIN FILM USING LASER-INDUCED BREAKDOWN SPECTROSCOPY

BACKGROUND OF THE INVENTION

1. Technical Field

The present disclosure relates to a fabrication processing system of a copper indium gallium selenide ($CuIn_{1-x}Ga_xSe_2$ or CIGS) thin film solar cell, more particularly to a fabrication processing system CIGS of thin film solar cell equipped with real-time analysis facilities for profiling the elemental components of CIGS thin film using laser-induced breakdown spectroscopy.

2. Description of the Related Art

Plasma generated at the time of laser irradiation emits light of a specific wavelength, so that an elemental components of a materials may be qualitatively and quantitatively analyzed using the collected light.

A laser-induced breakdown spectroscopy (hereafter referring to as LIBS), which is one method for analyzing a elemental component of the material using the collected light, is a spectral analysis techniques using plasma as an excitation source produced by generating a breakdown known as a discharge phenomenon.

A sample within the laser-induced plasma is vaporized such that atoms and ions may be present at exciting state.

The atoms and ions release energy after a certain lifetime and return back to a ground state to emit the specific wavelength based on a type of an element and the exited states. Therefore, by analyzing a spectrum of the emitted wavelength, the elemental components may be qualitatively and quantitatively analyzed.

FIG. 1 illustrates an operating principle of LIBS according to the prior art.

Referring to FIG. 1, first, as described in step 1, when a pulse laser is radiated to ablate a microscopic material (several μg) (The ablation refer to a phenomenon that a material is melted and vaporized by the laser to be removed), the ablated material absorbs laser energy, so that an ionization occurs during very short time and then forms high temperature plasma of about 15000K as described in step 2.

Upon termination of the laser pulse, the specific spectrum corresponding to each element within the plasma is generated while cooling the high temperature plasma. The spectrum generated at this time is collected and analyzed using a spectroscopy device to obtain a specific spectral data, so that the elemental element composition and the amount of the substance included within the material through a data analysis can be measured.

LIBS technique is different from other measurement technique in that:
1) the entire measuring time is within one second,
2) a separate sampling and pretreatment process for measurement is not required,
3) an element configuration of the material can be measured at an accuracy of mm unit while ablating the material in a depth direction due to requiring microscopic amount at one time measurement,
4) a measuring environment is not required and a measurement in air is possible, all elements is analyzed at ppm accuracy except inert gas, and
5) a facility is configured at a relatively low cost.

FIG. 2 is a chart comparing the different measurement.

Referring to FIG. 2, SIMS (Secondary Ion Mass Spectrometry), AES (Atomic Emission Spectroscopy), EDS (Energy Dispersive X-ray Spectroscopy), GD-MS (Glow Discharge Mass Spectrometry), which is commonly used in the measurement of the distribution of a material make measurement possible only in laboratory level due to the need of high vacuum, but they is not applicable to a line in reality.

In a widely used ICP-MS (Inductively Coupled Plasma-Mass Spectrometry, it is difficult that a sample piece to be analyze should be analyzed after is melted in a solvent, so that it is also impossible to apply to the fabrication line.

XRF (X-ray Fluorescence), which is widely used to a material analysis of the solar cell at a lab or on-site because of simplicity of use has a advantage that makes the measurement in air possible at low-cost, but, it is limited to the measurement for a material distribution of CIGS in that:
1) since the measurement for an lighter elements such as Na, O, N, C, B, Be, Li and the like is nearly possible, Na content measurement within CIGS thin film which has decisive effect on a element efficiency is impossible,
2) since a accuracy of a depth direction for XRF is merely up to about 1 μm, it is impossible that the measurement for the element distribution is implemented in a CIGS thin film of 2 μm in thick at depth direction, and
3) it is difficult to distinguish fluorescence signal whether a fluorescence signal output from the thin film or a from substrate. The prior art has a problem that the material distribution of the thin film is measured.

Generally, a semiconductor solar cell may be defined as element for converting sunlight directly into electricity using a photovoltaic effect generating electrons by radiating the light to the semiconductor having p-n junction.

A three parts, which is the most basic components, a front electrode, a rear electrode and a light absorbance layer disposed therebetween is formed.

The most important material is the light absorbance layer for determining the photoelectric conversion efficiency and the solar cell may be classified into several types.

This light absorbance layer material refers to CIGS thin film solar cell including $Cu(In,Ga)Se2$ of $I-III-VI_2$ compound. The CIGS thin film solar cell, which is the solar cell having high efficiency and low-cost type is most obviously noticed as second-generation cells to replace crystalline silicon cells and shows the efficiency closest to monocrtystalline device.

FIG. 3 illustrates schematically a structure of the thin solar cells.

FIG. 4 is a schematic flow chart showing a production process of the thin film module.

A CIGS thin film solar cell is manufactured by sequentially depositing MO layer, CIGS layer, CdS layer and TCO layer, which will be described in more detail as follows.

First, CIGS thin film module is manufactured by depositing Mo, which is a rear electrode layer on a substrate, sequentially depositing CIGS layer and CdS buffer layer, which is a light absorbance layer, on Mo layer, forming a pattern through a scribing process (P1 scribing), sequentially depositing TCO (transparent conductive oxide) layer and a front electrode grid of Ni/Al on CdS layer and finally performing the scribing process (P3 scribing).

The scribing process is a patterning process to be a serial connection in predetermined interval to prevent a reducing efficiency caused by a sheet resistance as a area resistance increases wherein the scribing process consists of a total of three times of P1, P2 and P3. Conventionally, P1 scribing is patterned by a laser and P2 and P3 scribing is patterned by a mechanical method, whereas recently the technique pattering all the P1, P2 and P3 using a laser has been developed.

In such a CIGS thin film solar cell, it is reported that a thickness of the thin film (1~2.2 μm), an elements structure, a composition of the material consisting of CIGS thin film, which is a pluralistic compound, and an element distribution within the thin film have an decisive effect on a light absorbance rate and a photoelectric conversion efficiency.

It is reported that sodium diffused on CIGS light absorbance layer from soda-lime grass is available generally as a substrate increases a charge density (Nakada et al., Jpn. J. Appl. Phys., 36, 732 (1997)) and increase CIGS single crystal grain size to reduce a properties change, thereby improving the photoelectric conversion efficiency (Rockett et al., Thin Solid Films 361-362 (2000), 330; Probst et al., Proc. of the First World Conf. on Photovoltaic Energy, Conversion (IEEE, New York, 1994), p. 144).

The reports suggest that chemical properties of the light absorbance layer should be controlled through the material distribution within the thin film to provide quality control in the production line of the CIGS thin film solar cell.

Meanwhile, a continuous production process of the CIGS thin film solar cells is classified into a roll-to plate (hereafter, referred to as R2P) process for utilizing a hardened material substrate such as soda-lime and a roll-to roll (hereafter, referred to as R2R) process for utilizing a metal sheet such as stainless steel, Ti, Mo, Cu and the like and a flexible material substrate of polymer and the like such as polyimide.

Since such a continuous production process is not provide with a system for measuring at real time physical and chemical properties of the CIGS thin film affecting on performance of the product on filling date, the inventor cannot help depending on the predetermined value for the physical and chemical properties described above.

In addition, a separate check are impossible even if the physical and chemical stands aiming at a actual production process is deviated and should be found through degradation of performance and quality to generate the loss of a significant product.

A considerable times and effort is taken to check the performance and quality of the products to check physical and chemical variables causing product performance and quality degradation to increase a price, thereby causing competitive degradation. It is preferable that a process control system that measures physical and chemical properties of CIGS thin film without pre-treatment in a real time is provided.

SUMMARY OF THE INVENTION

The object of the present invention is to provide a process control system for determining whether abnormalities are present or not by measuring a physical and chemical properties on a continuous production process lines of CIGS thin film solar cell in real time, and performing a production and quality management at the same time by providing a feedback to CIGS manufacturing process.

In order to achieve the object of the present invention, the present invention provides CIGS thin film solar cell fabrication process system including a object transfer section to continuously transfer a process object for manufacturing CIGS thin film solar cells; a thin film fabrication process section to perform CIGS thin film fabrication process on the process object during transfer; at least one header including at least one laser illustrating sectional to illustrate laser beam to CIGS thin film manufactured by the thin film fabrication process section and at least one spectroscopy detection section to detect the spectroscopy from a plasma generated CIGS thin film by the irradiated laser beam, a header transfer section combined with a transfer path of the object and the header in the same speed and direction as a moving speed and a moving direction of CIGS thin film manufactured by the thin film structure process section; a spectroscopy information storage section in which a spectroscopy state information is stored for each material; a spectroscopy analyzing section to analyze a material distribution state within the CIGS thin film from the spectroscopy detected by the a spectroscopy detection optical section based on the information stored in the spectroscopy information storage section; a process control section to control the thin film fabrication process section based on the material distribution state within CIGS thin film analyzed by the spectroscopy analyzing section; and a scribing section to pattern the CIGS thin film manufactured by a thin film fabrication process section.

In order to achieve the other object of the present invention, the present invention provides CIGS thin film solar cell fabrication process system including a object transfer section to continuously transfer a process object for manufacturing CIGS thin film solar cells; a thin film fabrication process section to perform CIGS thin film fabrication process on the process object during transfer; at least one header including a laser radiating sectional for at least one scribing to radiate a laser beam to pattern CIGS thin film manufactured by the thin film fabrication process, a spectroscopy detection optical section to detect a spectroscopy from plasma generated from CIGS by the radiated laser beam; a header transfer section combined with a transfer path of the object and the header in the same speed and direction as a moving speed and a moving direction of CIGS thin film manufactured by the thin film structure process section; a spectroscopy information storage section in which a spectroscopy state information is stored for each material; a spectroscopy analyzing section to analyze a material distribution state within the CIGS thin film from the spectroscopy detected by the a spectroscopy detection optical section based on the information stored in the spectroscopy information storage section; and a process control section to control the thin film fabrication process section based on the material distribution state within CIGS thin film analyzed by the spectroscopy analyzing section.

BRIEF DESCRIPTION OF THE DRAWINGS

FIG. 2 is a chart comparing between different measurement techniques.

FIG. 10 is illustrates in more detail laser radiating section in CIGS thin film solar cell fabrication process system according to a first embodiment (a) and a second embodiment (b) of the present invention.

FIG. 14 illustrates example that applies CIGS thin film solar electrode fabrication process system to R2R and R2P continuous production process according a first embodiment (a and b) and a second embodiment (c and d) of the present invention.

DESCRIPTION OF THE PREFERRED EMBODIMENTS

Figure 1:
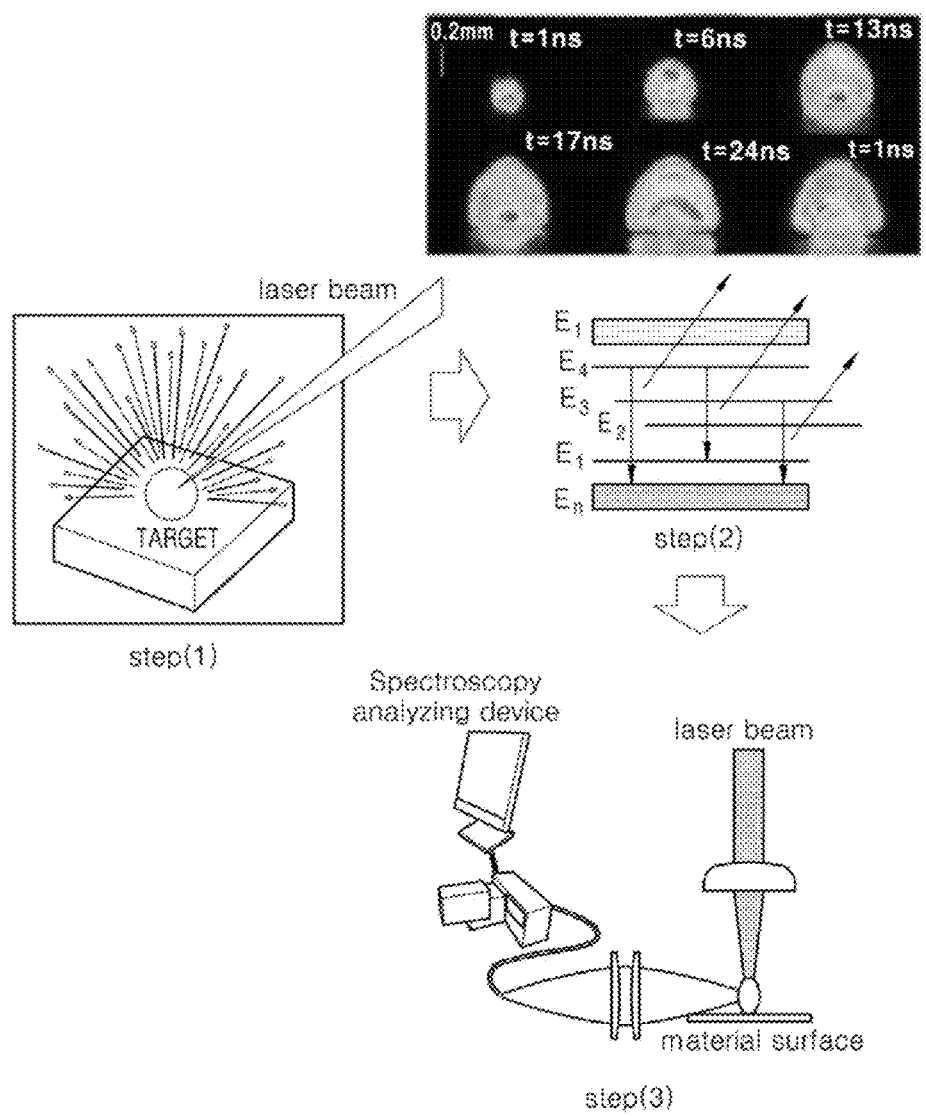
FIG. 1 illustrates an operating principle of LIBS.
Figure 3:
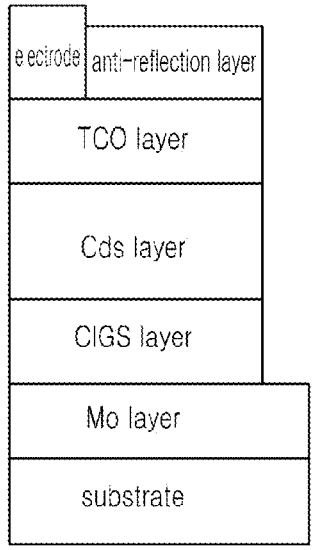
FIG. 3 illustrates a schematic structure of CIGS thin film solar cell.
Figure 4:
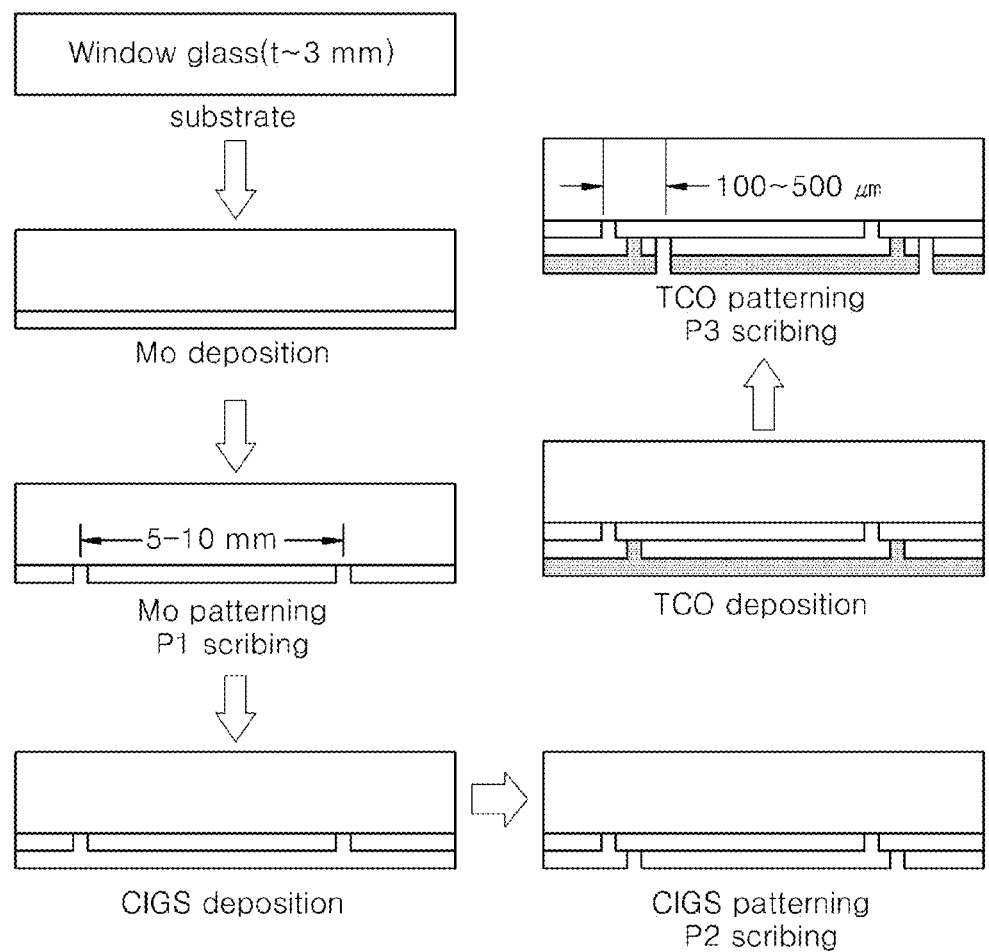
FIG. 4 is a schematic flowchart showing a fabrication process of CIGS thin film.

In the following detailed description, reference is made to the accompanying drawings that show, by way of illustration, specific embodiments in which the invention may be practiced. These embodiments are described in sufficient detail to enable those skilled in the art to practice the invention. It is to be understood that the various embodiments of the invention, although different from one another, are not necessarily mutually exclusive. For example, a particular feature, structure, and characteristic described herein in connection with one embodiment may be implemented within other embodiments without departing from the spirit and scope of the present invention. Also, it is to be understood that the locations or arrangements of individual elements in the embodiment may be changed without separating the spirit and scope of the present invention. The following detailed description is, therefore, not to be taken in a limiting sense, and the scope of the invention is defined only by the appended claims that should be appropriately interpreted along with the full range of equivalents to which the claims are entitled. In the drawings, like reference numerals identify identical or like elements or functions through the several views. In the specification, "one embodiment" means that components, shapes, characteristics, principles, or the like, used in the corresponding embodiment may also be used other embodiments.

Hereinafter, the configuration of the present invention will be described in detail with reference to the accompanying drawings so that those skilled in the art can easily carry out the present invention.

While the invention has been shown and described with respect to the particular embodiments, it will be understood by those skilled in the art that various changes and modification may be made without departing from the spirit and scope of the invention as defined in the following claims.

(First Embodiment)

Figure 5A:
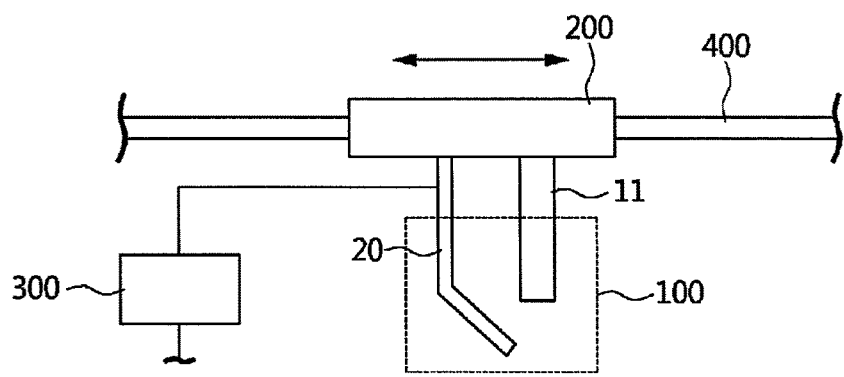
FIG. 5 illustrates a fabrication process system of CIGS thin film solar cell according to a first embodiment of the present invention.
Figure 5B:
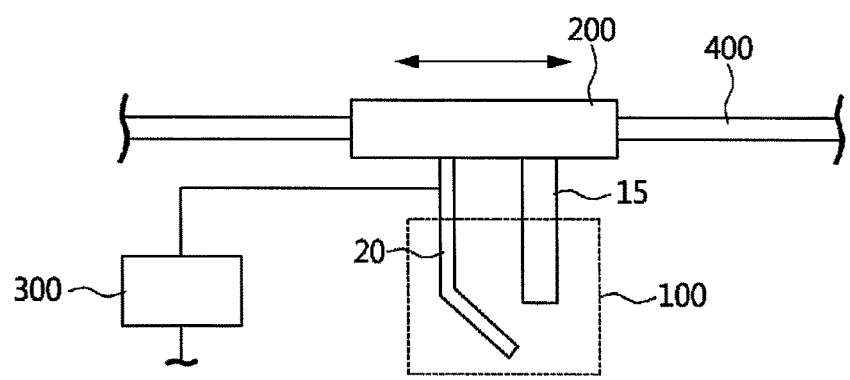
Figure 6:
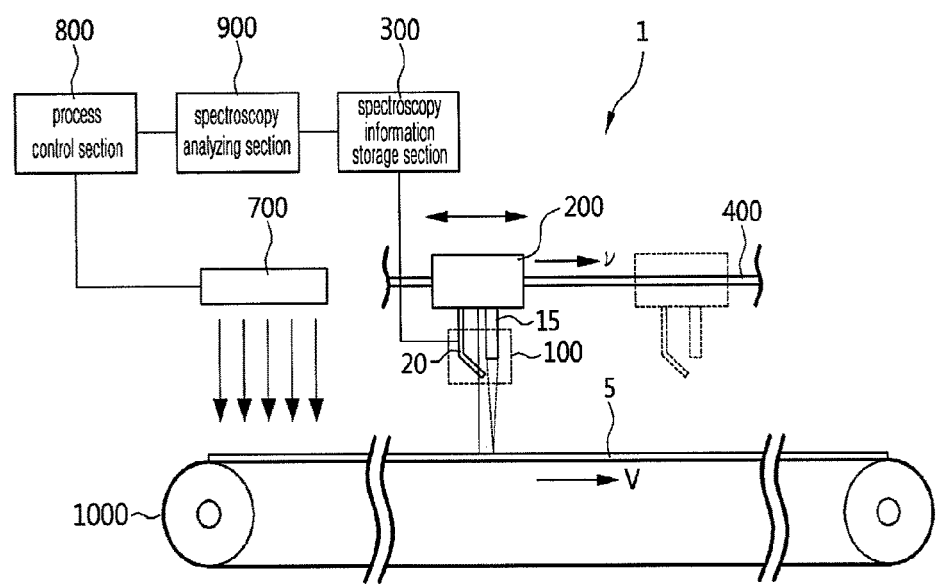
FIG. 6 illustrates a fabrication process system of CIGS thin film solar cell according to a second embodiment of the present invention.

FIG. 5 shows CIGS thin film solar electrode fabrication process system according to an embodiment of the present disclosure. FIG. 6 illustrates a fabrication process system of CIGS thin film solar cell. The components in FIG. 6 will be referenced with respect to the operation of the components in FIGS. 5 and 7-11.

Referring to FIGS. 5 and 6, CIGS thin film solar electrode fabrication process system of the present invention includes a object transfer section 1000, a thin film fabrication processing section 700, a header 100, a header transfer section 200, a spectroscopy information storage section 300, a spectroscopy analyzing section 900, a process control section 800 and scribing section 600.

When a process object is continuously transferred by the object transfer section 110, CIGS layer is deposited on the process object by the thin film fabrication section 700.

A CIGS thin film 5 that a deposition process of CIGS layer on the layer is finished is continuously transferred by the object transfer section 1000.

The header 100 serves to radiate a laser beam to CIGS thin film 5 transferred by the object transfer section 1000 and to detect a spectroscopy of plasma generated from CIGS thin film.

The header 100 is coupled to a lower end of the header transfer section 200.

The header transfer section 200 transfers the header 100 in interlock with CIGS thin film 5 transferred continuously by the object transfer section 1000.

Therefore, the header 100 is transferred in interlock with CIGS thin film 5 together with depending on the transfer of the header transfer section 200.

The spectroscopy information storage section 300 stores a spectroscopy state information that build a data base and the spectroscopy analyzing section 900 analyzes the spectroscopy information transferred from the header 100 based on a information of the spectroscopy information storage section 300 and senses whether an abnormality of a chemical or physical distribution of the material including CIGS thin film 5 is present or not.

If the process control section 700 senses whether the abnormality of the spectroscopy analyzing section 900 is present or not, a ratio and distribution of the elements is adjusted to be constant and provides a feedback on the thin film fabrication process section 700.

If the process control section 700 senses that the spectroscopy analyzing section 900 is normal, CIGS thin film 5 manufactured by the thin film fabrication process section 700 is scribed by the scribing section 600 and then is transferred to the following process.

The object transfer section 1000 continuously moves the process object for fabrication the CIGS thin film solar cell.

The process object may has different designations such as a substrate, Mo layer-deposited substrate, CIGS thin film and the like according to a progress of the process of CIGS thin film solar cell.

In the specification, the process object includes CIGS thin film 5 and CIGS thin film 5 performs P1 scribing during the production of CIGS thin film solar cell and then CIGS layer means a deposited process object.

If CIGS thin film solar cell fabrication process system proceeds to R2P or R2R, the object transfer section 1000 is operated by a roll formed in both ends of CIGS solar cell fabrication process system.

In particular, the object transfer section 1000 may be a conveyor belt.

The thin film fabrication process section 700 is a element for CIGS thin film fabrication process included within CIGS thin film solar cell, wherein the process associated with the CIGS thin film solar cell may be correspond thereto.

In particular, the CIGS thin film fabrication process may be a CIGS deposition process and the thin film fabrication process section 700 may be a sputter.

The header 100 and the header transfer section 200 will be described in a detail with reference to FIG. 7a.

The spectroscopy information storage 300 may store a spectroscopy state for each material of information which builds a database.

The spectroscopy information storage 300 may include information associated with a spectroscopy corresponding to each material including CIGS thin film, that is, information associated with a spectroscopy corresponding to each material including the standard object as preferably manufactured CIGS thin film.

The spectroscopy analyzing section 900 is connected to the header 100. In more detail, the spectroscopy analyzing section 900 is electrically connected to the spectroscopy detection optical section 20 including the header 100 to analyze the spectroscopy sensed from the spectroscopy detection optical section 20.

For example, if the spectroscopy sensed from the spectroscopy detection optical section 20 includes specific LIBS intensity information, the spectroscopy analyzing section 900 analyzes the information to perceive the rate and distribution of the element of the CIGS thin film 5 and to determine an error of suitability of chemical composition or physical distribution of manufactured CIGS thin film 5.

The scribing section 600 forms a uniform pattern on CIGS thin film 5 manufactured normally by the thin film fabrication process section 700, wherein the scribing section may a structure for P2 scribing process during the manufacture of CIGS thin film module. In particular, the scribing 600 may perform laser scribing including a scribing laser.

The process control section 800 is a structure to uniform the rate and distribution of the element including CIGS thin film 5 based on the material distribution state within CIGS thin film 5 analyzed the spectroscopy analyzing section 900 to provide a feedback on the thin film fabrication process section 700.

If there is no a abnormality in material distribution state within CIGS thin film analyzed by the spectroscopy analyzing section 900, a subsequent process such as P2 scribing by the scribing section 600 proceed, whereas, if there is a abnormality in material distribution state within CIGS thin film 5 analyzed by the spectroscopy analyzing section 900, a value of the rate and distribution of element in the process control section 600 is modified and input back to the thin film fabrication process section 700 and the thin film process section 700 manufactures CIGS thin film 5, more preferably deposits CIGS based on the modified value.

Figure 7A:
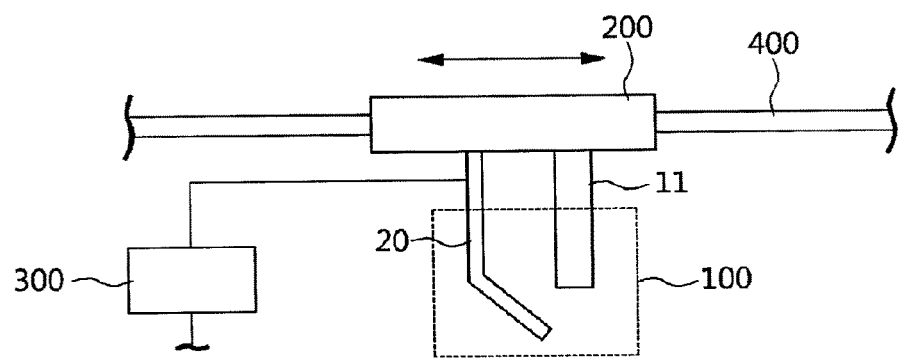
FIG. 7 is an illustrating view showing an emerged header and a header transfer section in CIGS thin film solar cell fabrication process system according a first embodiment (a) and a second embodiment (b) of the present invention.

FIG. 7A illustrates an enlarged header and a header transfer section in CIGS thin film solar cell fabrication process system according to a first embodiment of the present invention.

Referring to FIG. 7A, the header 100 includes a laser radiating section 11 and the spectroscopy detection optical section 20.

The laser radiating section 11 is connected to the header transfer section 200 and radiates a specific laser the CIGS thin film 5.

A kind of laser beam output from the laser radiating section 11 may be appropriately selected based on the properties of the produced CIGS thin film 5 by those having ordinary art.

Plasma is generated from the CIGS thin film 5 by the radiation of the laser beam using the laser radiating section 11.

In particular, it is preferable that the laser beam radiated according to the material and the chemical composition of CIGS thin film 5 is appropriately selected to facilitate the ablation of the CIGS thin film 5.

The spectroscopy detection optical section 20 is connected to the header transfer section 200 and is disposed adjacent to laser radiating section 11.

In particular, preferably, the spectroscopy detection optical section is disposed at appropriate position to sense the spectroscopy component of the plasma generated from CIGS thin film 5.

The spectroscopy detection optical section 20 can utilize all the optical section capable of detecting the spectroscopy generated from the plasma, for example, an echelle spectroscopy such as high-precision optical instruments, Intensified Charge Coupled Devide (ICCD) and the like.

The header transfer section 200 is transfer in interlock with the transfer of the CIGS thin film. For example, if CIGS thin film 5 horizontally move in a specific direction, the header transfer section 200 transfers at the same speed (V) and direction (D) as those of the CIGS thin film 5 with together, and simultaneously disposes the header 100 on CIGS thin film 5 to radiate continuously the laser beam at the same position CIGS thin film 5 during transfer and to detect the spectroscopy.

Figure 8A:
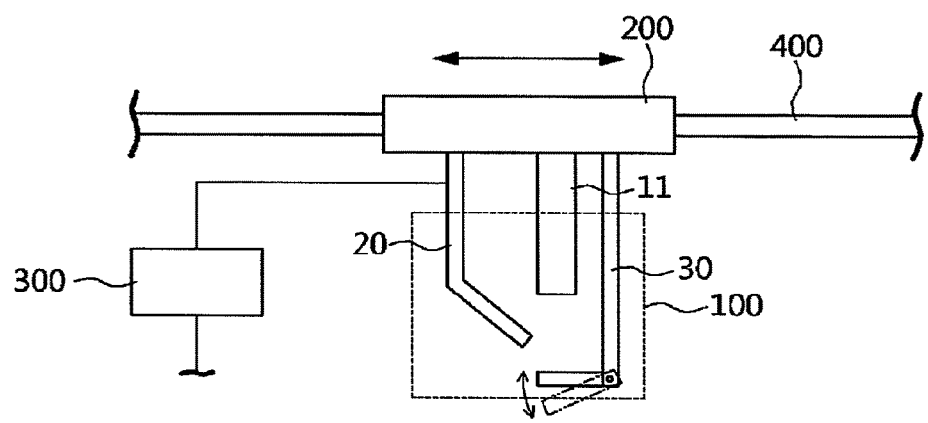
FIG. 8 is an illustrating view a header and header transfer section additionally provided with beam irradiation positioning section in CIGS thin film solar cell fabrication process system according a first embodiment (a) and a second embodiment (b) of the present invention.

FIG. 8A is illustrates the enlarged header and the header transfer provided additionally with the beam irradiation positioning section in CIGS thin film solar cell solar cell fabrication process according to a first embodiment of the present invention.

Referring to FIG. 8A, The CIGS thin film solar cell fabrication process system shown FIG. 8A has the same component as FIG. 8A and adds the beam radiating positioning section to the header 100.

The beam irradiation positioning section 30 finely adjusts the position in which the laser beam radiates at state that the laser radiating section 11 is fixed to the header transfer section 200.

That is, a radiating position of the laser beam is primarily set in accordance to the transfer of the header transfer section 200.

In addition, if the adjustment of the fine radiating position is required at position that the header transfer section 200 is set, the beam irradiation section 30 is adjustable radiating position of the laser beam by adjusting the angle of incidence.

For example, in FIG. 8A, in the beam irradiation positioning section 30 disposed in form of " ⌐ ", a horizontal portion to the header transfer section 200 is consist of a reflector and the radiating position of the laser beam is adjusted through angle adjustment of the reflector.

In FIG. 8A expressing the real time measurement system as a side view, the reflector which is a horizontal portion to the header transfer section 200 can be moved up and down and the reflector can be moved in every direction.

The laser beam radiating position may be secondarily adjusted through the introduction of the beam irradiation positioning section 30 and in particular the beam irradiation positioning section 30 may a 'galvanc meter' available in field of the art. The galvanic meter performs a fine adjustment of the laser beam by a reciprocating or rotary motion of the reflector of radiated laser beam.

Figure 9A:
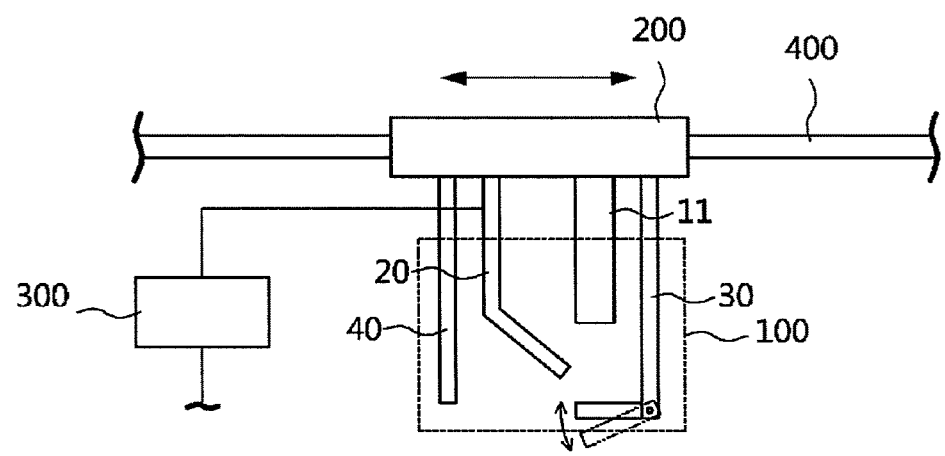
FIG. 9 is an illustrating view showing an a header and a header transfer sectional provided additionally with an index recognition section in CIGS thin film solar cell fabrication process system according to a first embodiment (a) and a second embodiment (b) of the present invention.

FIG. 9A is an illustrating view showing a enlarged header and a header transfer section provided additionally with an index recognition optical section in CIGS thin film solar fabrication process system according to a first embodiment of the present invention.

Referring to FIG. 9A, CIGS thin film solar cell fabrication process system has the same component shown in FIG. 8A and adds the index recognition optical section 40 to the header 100.

Therefore, the description for the same component as FIG. 7A and FIG. 8A are omitted and will be described with regard to additive the index recognition optical section.

The index recognition optical section 40 is connected to the header transfer section 200.

The index recognition optical section 40 may be an element referred to as 'vision' in the art.

An image of the CIGS thin film 5 captures a surface image of the CIGS thin film 5 at a captured or stored state and compares with the surface image of the stored CIGS thin film 5 to determine the position in which the laser beam radiates.

The position in which the laser beam is radiated within the CIGS thin film 5 may be determined through the index recognition optical section 40, so that the laser beam can be radiated at the position in which user wants.

FIG. 10A illustrates a laser irradiation section the CIGS thin film solar cell fabrication process system according to a first embodiment of the present invention.

Referring to FIG. 10A, the layer irradiation section includes a laser section for ablation 111 and an auto-focus section 121.

The laser section for ablation 111 generates the laser beam or transfers the generated laser beam to auto-focus section 121.

In particular, All kind of the laser ablating the CIGS thin film 5 may be used within the laser section for ablation but any one laser selected from group consisting of ND:YAG laser, Nd:YLF laser and ND:YV04 laser is preferably used within the laser section for ablation.

In particular, ND:YAG laser may be used within the laser section for ablation 111. In addition, the auto-focus section 121 adjusts the focus of the laser beam provided from the laser section for ablation 111.

In particular, the laser beam focus may be automatically adjusts through the auto-focus section 121.

For this, even if sensing device is not shown in FIGS. 7A, 8A and 9A, a sensing device for sensing a focus of the laser beam is further provided, so that, the auto-focus section can adjust the focus of laser beam using the focus information transferred through the sensing advice.

In addition, the irradiation position of the laser beam can be adjusted in the range of −180 degree to +180 degree based on the same direction (d) as the moving direction of the CIGS thin film (M) and the moving direction (D) of the CIGS thin film by adjusting a angle of the reflector of the beam irradiation positioning section 30 described in FIGS. 8A and 9A.

Figure 11:
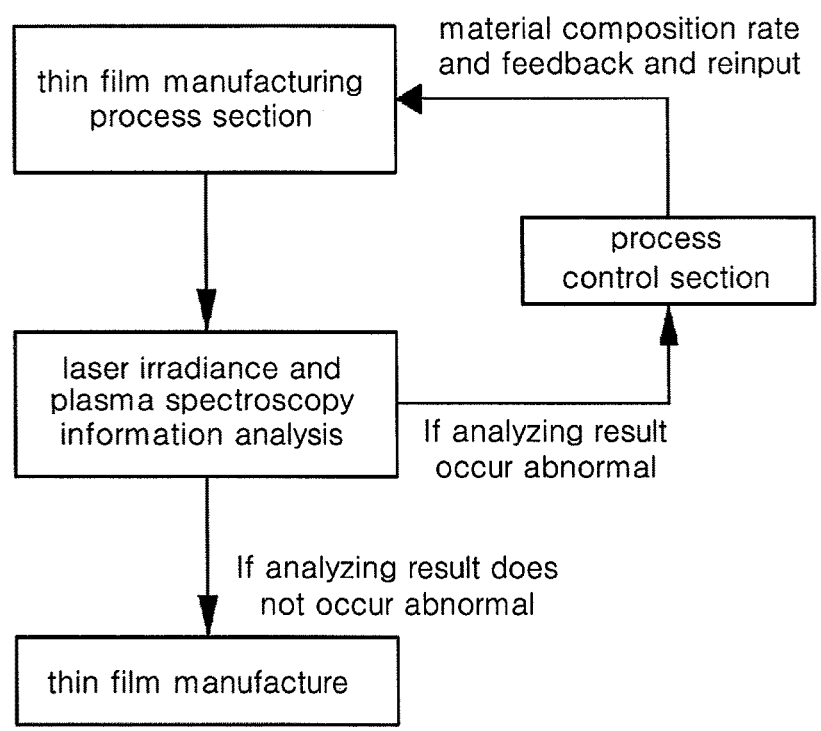
FIG. 11 is flowchart showing an operating principle of CIGS solar cell thin film fabrication process system according to a first embodiment and a second embodiment of the present invention.

FIG. 11 is flowchart showing the operating principle of CIGS thin film solar cell fabrication process system according to a first and second embodiment of the present invention.

Referring to FIG. 6, as well as FIG. 11, if there is no a abnormality in material distribution state within CIGS thin film analyzed by the spectroscopy analyzing section 900, a subsequent process such as P2 scribing by the scribing section 600 proceed, whereas, if there is a abnormality in material distribution state within CIGS thin film analyzed by the spectroscopy analyzing section 900, a value of the rate and distribution of element in the process control section 800 is modified and input back to the thin film fabrication process section 700 and the thin film process section 700 manufactures CIGS thin film 5, more preferably deposits CIGS based on the modified value.

Figure 12:
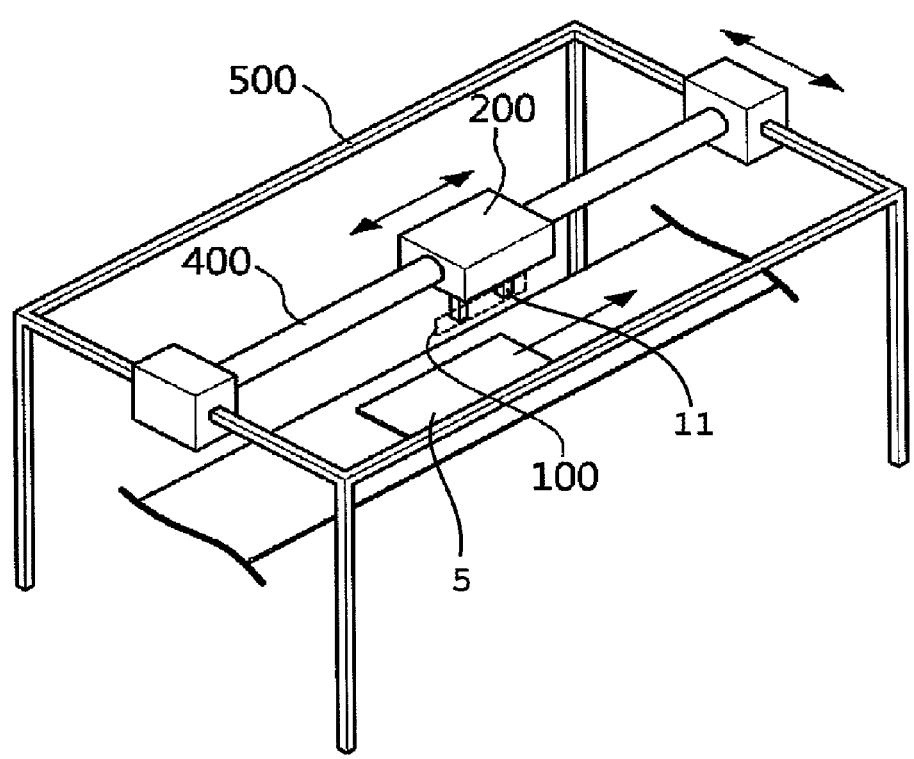
FIG. 12 is an illustrating view an operation of a header and transfer section in CIGS thin film solar cell fabrication process system according to a first embodiment and a second embodiment of the present invention.

FIG. 12 illustrates a operation of the header and the header transfer section in CIGS thin film solar cell fabrication process system according a first or second embodiment of the present invention.

Referring to FIG. 12, the header transfer section 200 transfers the header 100 in the same direction (d) as the moving direction (D) of the CIGS thin film 5 and the same speed (v) as the moving speed (V) of the CIGS thin film 5. Therefore, the laser irradiation section 11 and the spectroscopy detection section and the like including the header 100 is transferred in the same speed and direction as the moving speed (V) of the CIGS thin film 5.

The header transfer section 200 is transferred in the same direction as the moving direction (D) of the CIGS thin film 5 in the fixed platform 500 along a transfer path 400.

The header transfer path 400 may be moved in direction perpendicular to the moving direction (D) of the CIGS thin film 5 on the fixed platform 500, the header transfer path 400 may be moved in a direction perpendicular to the moving direction of the CIGS thin film 5 to be moved in direction perpendicular to the moving direction (D) of header 100 or CIGS thin film 5.

That is, the irradiation position of the layer beam radiated from the laser irradiation section 11 may be global positioning by the header transfer path 400 movable perpendicular to the moving direction (D) of CIGS thin film 5 and the header transfer section 200.

Figure 13A:
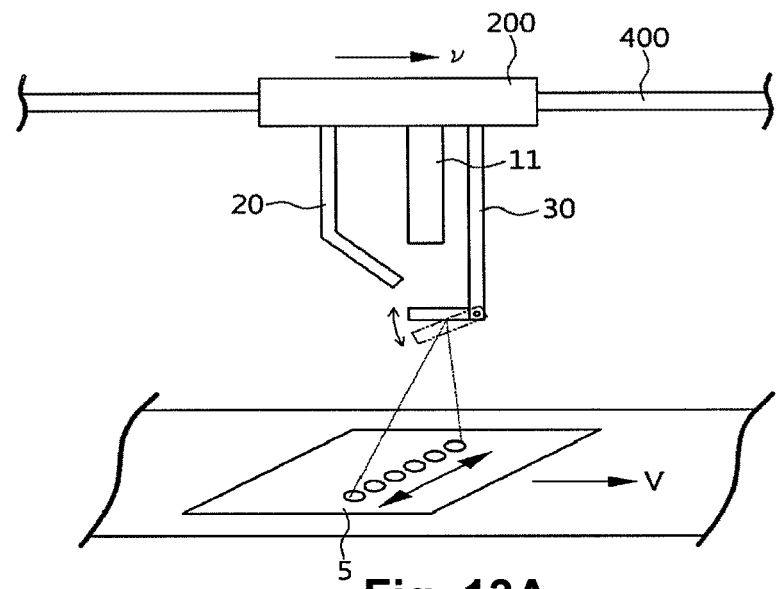
FIG. 13 is an illustrating view for explaining an operating principle that a laser beam position is adjusted fine by the beam irradiation positioning section in CIGS thin film solar cell fabrication process system according a first embodiment (a) and a second embodiment (b) of the present invention.

FIG. 13A is illustrates the principle in which the laser beam position is adjusted by the beam irradiation positioning section in CIGS thin film solar cell fabrication process system according to a first embodiment of the present invention.

Referring FIG. 13A, the irradiation position of the laser beam can be adjusted in the range of −180 degree to +180 degree based on the same direction (d) as the moving direction (D) of the CIGS thin film (M) and the moving direction (D) of the CIGS thin film by adjusting a angle of the reflector of the beam irradiation positioning section 30 described.

This is adjustable in direction of −90° and +90° based on the moving direction (D) of the CIGS thin film but is limited to this in FIG. 10.

FIGS. 14A and B illustrates an example that CIGS thin film solar cell fabrication process system is applied to R2R and R2P according to a first embodiment of the present invention.

Referring FIGS. 14A and B, a real time measurement system S of the CIGS thin film material distribution may be applied to (a) R2R or (b) R2P process, which is continuous process.

The kind of process is different according to the kind of substrate used to CIGS thin film 5 manufactured by the kind of process.

The CIGS thin film 5 applies the real time measurement system (S) of CIGS thin film material distribution to a process R2P using hardened material substrate such as soda-lime.

Meanwhile, a continuous production process of the CIGS thin film solar cells is classified into a roll-to plate (hereafter, referred to as R2P) process for utilizing a hardened material plate such as soda-lime and a roll-to roll (hereafter, referred to as R2R) process for utilizing a metal sheet such as stainless steel, Ti, Mo, Cu and the like and a flexible material substrate of polymer and the like such as polyimide.

On the other hand, the CIGS thin film 5 applies the real time measurement system (S) of the CIGS thin film material distribution to R2R process using a metal sheet such as stainless steel, Ti, Mo, Cu and the like and a flexible material substrate of polymer and the like such as polyimide.

(Second Embodiment)

FIG. 6 illustrates CIGS thin film solar cell fabrication process system according to a second embodiment of the present invention.

Referring to 6, CIGS thin film solar electrode fabrication process system of the present invention includes a object transfer section 1000, a thin film fabrication processing section 700, a header 100, a header transfer section 200, a spectroscopy information storage 300, a spectroscopy analyzing section 900, a process control section 800.

When a process object is continuously transferred by the object transfer section 110, CIGS layer is deposited on the process object by the thin film fabrication section 700.

CIGS thin film 5 that a deposition process of CIGS layer on the layer is finished is continuously transferred by the object transfer section 1000.

The header 100 serves to radiate a laser beam to CIGS thin film 5 transferred by the object transfer section 1000 to perform a scribing process and to detect a spectroscopy of a plasma generated from CIGS thin film to be scribing.

The header 100 is coupled to a lower end of the header transfer section 200.

The header transfer section 200 transfers the header 100 in interlock with CIGS thin film 5 transferred continuously by the object transfer section 1000 together with.

Therefore, the header 100 is transferred in interlock with CIGS thin film 5 depending on the transfer of the header transfer section 200 together.

The spectroscopy information storage section 300 stores a spectroscopy state information that builds a data base and the spectroscopy analyzing section 900 analyzes the spectroscopy information transferred from the header 100 based on information of the spectroscopy information storage section 300 and senses whether a abnormality of a chemical or physical distribution of the material including CIGS thin film 5 is present or not.

If the process control section 700 senses whether the abnormality of the to spectroscopy analyzing section 900 is present or not, a ratio and distribution of the elements is adjusted to be constant and provides a feedback on the thin film fabrication process section 700.

If the process control section 700 senses that the spectroscopy analyzing section 900 is normal, CIGS thin film manufactured by the thin film fabrication process section 700 is transferred to the following such as process TCO layer deposition at the transfer section 1000.

The object transfer section 1000 continuously moves the process object for manufacturing the CIGS thin film solar cell.

The process object may has different designations such as a substrate, Mo layer-deposited substrate, CIGS thin film and the like according to a progress of the process of CIGS thin film solar cell.

In the specification, the process object includes CIGS thin film 5 and CIGS thin film 5 performs P1 scribing during the production of CIGS thin film solar cell and then CIGS layer means a deposited process object.

If CIGS thin film solar cell fabrication process system proceeds to R2P or R2R, the object transfer section 1000 is operated by a roll formed in both ends of CIGS solar cell fabrication process system.

In particular, the object transfer section 1000 may be a conveyor belt.

The thin film fabrication process section 700 is a element for CIGS thin film fabrication process included within CIGS thin film solar cell, wherein the process associated with the CIGS thin film solar cell may be correspond thereto.

In particular, the CIGS thin film fabrication process may be a CIGS deposition process and the thin film fabrication process section 700 may be a sputter.

The header 100 and the header transfer section 200 will be described in a detail with reference to FIG. 7B The spectroscopy information storage 300 may store a spectroscopy state for each material of information which builds a database.

The spectroscopy information storage 300 may include information associated with a spectroscopy corresponding to each material including CIGS thin film, that is, information associated with a spectroscopy corresponding to each material including the standard object as preferably manufactured CIGS thin film.

The spectroscopy analyzing section 900 is connected to the header 100. In more detail, the spectroscopy analyzing section 900 is electrically connected to the spectroscopy detection optical section 20 including the header 100 to analyze the spectroscopy sensed from the spectroscopy detection optical section 20.

For example, if the spectroscopy sensed from the spectroscopy detection optical section 20 includes specific LIBS intensity information, the spectroscopy analyzing section 900 analyzes the information to perceive the rate and distribution of the element of the CIGS thin film 5 and to determine an error of suitability of chemical composition or physical distribution of manufactured CIGS thin film 5.

The process control section 800 is a structure to uniform the rate and distribution of the element including CIGS thin film 5 based on the material distribution state within CIGS thin film 5 analyzed the spectroscopy analyzing section 900 to provide a feedback on the thin film fabrication process section 700.

If there is no a abnormality in material distribution state within CIGS thin film analyzed by the spectroscopy analyzing section 900, a subsequent process such as TCO deposition layer proceed, whereas, if there is a abnormality in material distribution state within CIGS thin film 5 analyzed by the spectroscopy analyzing section 900, a value of the rate and distribution of element in the process control section 800 is modified and input back to the thin film fabrication process section 700 and the thin film process section 700 manufactures CIGS thin film 5, more preferably deposits CIGS based on the modified value.

Figure 7B:
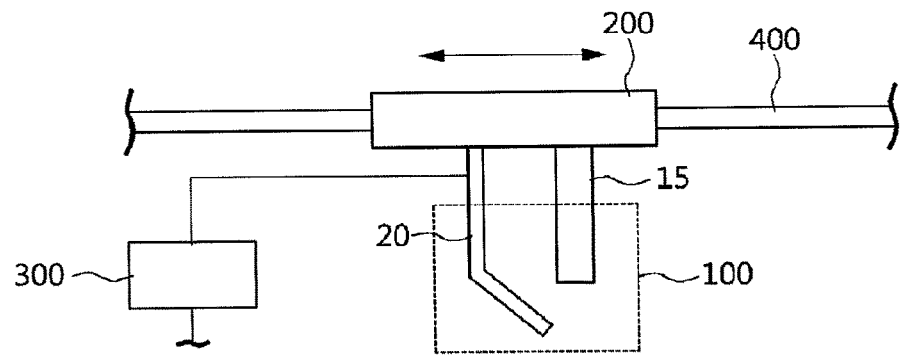

FIG. 7B illustrates an enlarged header and a header transfer section in CIGS thin film solar cell fabrication process system according to a second embodiment of the present invention.

Referring to FIG. 7B, the header 100 includes a laser radiating section 11 and the spectroscopy detection optical section 20.

The laser radiating section 15 is connected to the header transfer section 200 and radiates a specific laser the CIGS thin film 5.

A kind of laser beam output from the laser radiating section may be appropriately selected based on the properties of the produced CIGS thin film 5 by those skilled in the art.

Plasma is generated from the CIGS thin film 5 by the radiation of the laser beam using the laser radiating section.

In particular, it is preferable that the laser beam radiated according to the material and the chemical composition of CIGS thin film 5 is appropriately selected to facilitate the ablation of the CIGS thin film 5.

The spectroscopy detection optical section 20 is connected to the header transfer section 200 and is disposed adjacent to laser radiating section 15.

In particular, preferably, the spectroscopy detection optical section is disposed at appropriate position to sense the spectroscopy component of the plasma generated from CIGS thin film 5.

The spectroscopy detection optical section 20 can utilize all the optical section capable of detecting the spectroscopy generated from the plasma, for example, an echelle spectroscopy such as high-precision optical instruments, Intensified Charge Coupled Devide (ICCD) and the like.

The header transfer section 200 is transferred in interlock with the transfer of the CIGS thin film. For example, if CIGS thin film 5 horizontally move in a specific direction, the header transfer section 200 transfers at the same speed (V) and direction (D) as those of the CIGS thin film 5 with together, and simultaneously disposes the header 100 on CIGS thin film 5 to radiate continuously the laser beam at the same position CIGS thin film 5 during transfer and to detect the spectroscopy.

Figure 8B:
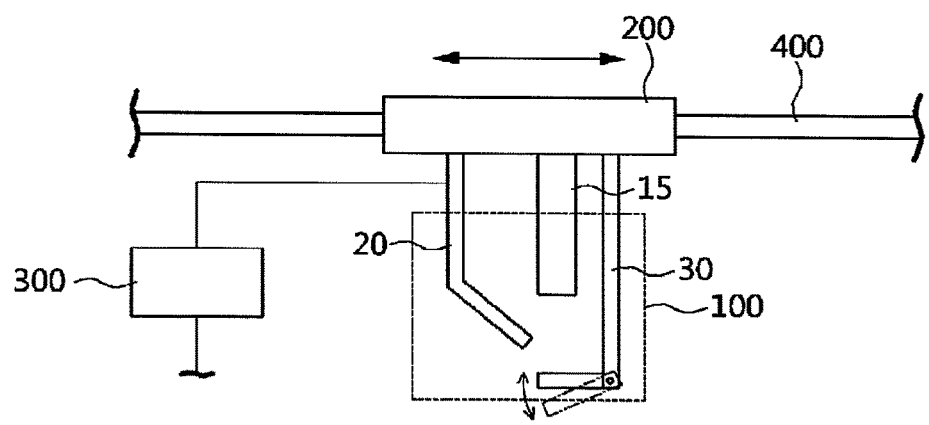

FIG. 8B illustrates the enlarged header and the header transfer provided additionally with the beam irradiation positioning section in CIGS thin film solar cell according to a first embodiment of the present invention.

Referring to FIG. 8B, The CIGS thin film solar cell fabrication process system shown in FIG. 8B has the same component as FIG. 7B and adds the beam irradiation positioning section 30 to the header 100.

The irradiation positioning section 30 finely adjusts the position in which the laser beam is radiated at state that the laser radiating section 11 is fixed to the header transfer section 200.

That is, a radiating position of the laser beam is primarily set in accordance to the transfer of the header transfer section 200.

In addition, if the adjustment of the fine radiating position is required at position that the header transfer section 200 is set, the beam irradiation section 30 adjusts radiating position of the laser beam by adjusting the angle of incidence.

For example, in FIG. 8B, in the beam irradiation positioning section 30 disposed in form of " ⌐ ", a horizontal portion to the header transfer section 200 is consist of a reflector and the radiating position of the laser beam is adjusted through angle adjustment of the reflector.

In FIG. 8B expressing the real time measurement system as a side view, the reflector which is a horizontal portion to the header transfer section 200 can be moved up and down and the reflector can be moved in every direction.

The laser beam radiating position may be secondarily adjusted through the introduction of the beam irradiation positioning section 30 and in particular, the beam irradiation positioning section 30 may a 'galvanic meter' available in the art. The galvanic meter performs a fine adjustment of the laser beam by a reciprocating or rotary motion of the reflector of radiated laser beam.

Figure 9B:
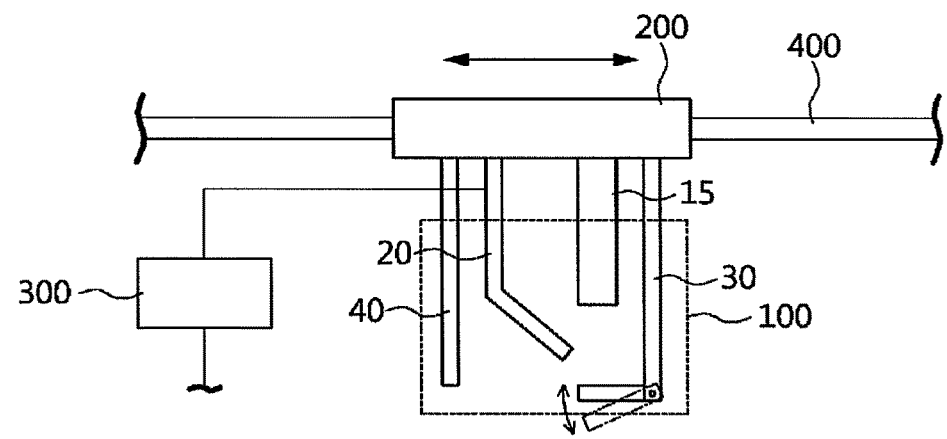

FIG. 9B is an illustrating view showing a enlarged header and a header transfer section provided additionally with an index recognition optical section in CIGS thin film solar fabrication process system according to a second embodiment of the present invention.

Referring to FIG. 9B, CIGS thin film solar cell fabrication process system has the same component shown in FIG. 8B and adds the index recognition optical section 40 to the header 100.

Therefore, the description for the same component as FIG. 7B and FIG. 8A is omitted and will be described with regard to additive index recognition optical section.

The index recognition optical section 40 is connected to the header transfer section 200.

The index recognition optical section 40 may be an element referred to as 'vision' in the art.

An image of the CIGS thin film 5 captures a surface image of the CIGS thin film 5 at a captured or stored state and compares with the surface image of the stored CIGS thin film 5 to determine the position in which the laser beam radiates.

The position in which the laser beam is radiated within the CIGS thin film 5 may be determined through the index recognition optical section 40, so that the laser beam can be radiated at the position in which user wants.

FIG. 10B illustrates a laser irradiation section the CIGS thin film solar cell fabrication process system according to a second embodiment of the present invention in detail.

Referring to FIG. 10B, the layer irradiation section includes a laser section for ablation 115 and an auto-focus section 125.

The laser section for scribing 115 generates the laser beam or transfers the generated laser beam to auto-focus section 125.

In particular, all kind of the laser scribing the CIGS thin film 5 may be used within the laser section for scribing 115 but any one laser selected from group consisting of ND:YAG laser, Nd:YLF laser and ND:YV04 laser is preferably used within the laser section for scribing.

In particular, ND:YAG laser may be used within the laser section for scribing 115. In addition, the auto-focus section 125 adjusts the focus of the laser beam provided from the laser section for scribing 115.

In particular, the laser beam focus may be automatically adjusted through the auto-focus section 125.

For this, even if sensing device is not shown in FIGS. 7B, 8B and 9B, a sensing device for sensing a focus of the laser beam is further provided, so that the auto-focus section 125 can adjust the focus of laser beam using the focus information transferred through the sensing advice.

In addition, the irradiation position of the laser beam can be adjusted in the range of −180 degree to +180 degree based on the same direction (d) as the moving direction of the CIGS thin film (M) and the moving direction (D) of the CIGS thin film by adjusting a angle of the reflector of the beam irradiation positioning section 30 described FIGS. 8B and 9B.

FIG. 11 is flowchart showing the operating principle of CIGS thin film solar cell fabrication process system according to a first and second embodiment of the present invention.

Referring to FIG. 11, if there is no a abnormality in material distribution state within CIGS thin film analyzed by the spectroscopy analyzing section 900, a subsequent process such as TCO layer deposition proceeds, whereas, if there is a abnormality in material distribution state within CIGS thin film 5 analyzed by the spectroscopy analyzing section 900, a value of the rate and distribution of element in the process control section 800 is modified and input back to the thin film fabrication process section 700 and the thin film process section 700 manufactures CIGS thin film 5, more preferably deposits CIGS based on the modified value.

FIG. 12 illustrates an operation of the header and the header transfer section in CIGS thin film solar cell fabrication process system according a first and second embodiment of the present invention.

Referring to FIG. 12, the header transfer section 200 transfers the header 100 in the same direction (d) as the moving direction (D) of the CIGS thin film 5 and the same speed (v) as the moving speed (V) of the CIGS thin film 5. Therefore, the laser irradiation section 11 and the spectroscopy detection section 20 and the like including the header 100 is transferred in the same speed and direction as the moving speed (V) of the CIGS thin film 5.

The header transfer section 200 is transferred in the same direction as the moving direction (D) of the CIGS thin film 5 in the fixed platform 500 along a transfer path 400.

The header transfer path 400 may be moved in direction perpendicular to the moving direction (D) of the CIGS thin film 5 on the fixed platform 500, and the header transfer path 400 may be moved in a direction perpendicular to the moving direction of the CIGS thin film 5 to be moved in direction perpendicular to the moving direction (D) of header 100 or CIGS thin film 5.

That is, the irradiation position 15 of the layer beam radiated from the laser irradiation section may be global positioning by the header transfer path 400 movable perpendicular to the moving direction (D) of CIGS thin film 5 and the header transfer section 200.

Figure 13B:
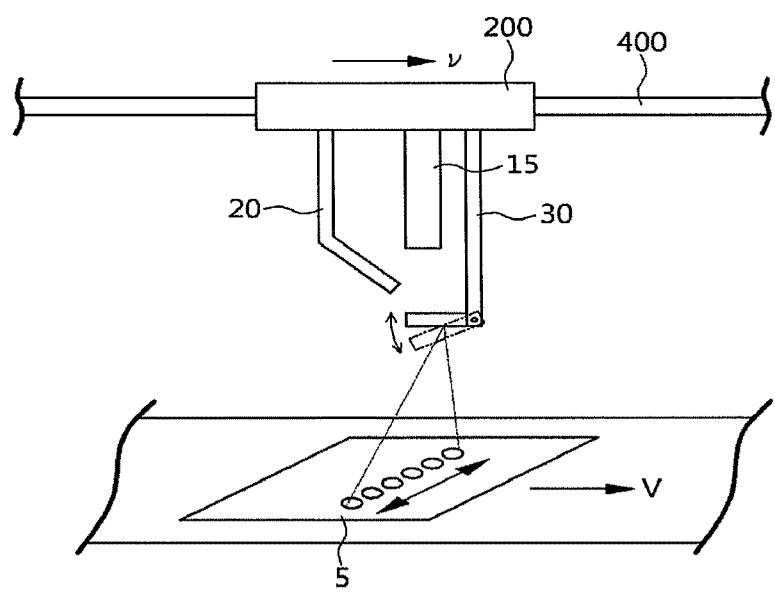

FIG. 13B is illustrates the principle in which the laser beam position is adjusted by the beam irradiation positioning section in CIGS thin film solar cell fabrication process system according to a second embodiment of the present invention.

Referring FIG. 13B, the irradiation position of the laser beam can be adjusted in the range of −180 degree to +180 degree based on the same direction (d) as the moving direction (D) of the CIGS thin film (M) and the moving direction (D) of the CIGS thin film by adjusting a angle of the reflector of the beam irradiation positioning section 30 described.

This is adjustable in direction of −90° and +90° based on the moving direction (D) of the CIGS thin film but is not limited to this in FIG. 10.

FIGS. 14C and D illustrates an example that CIGS thin film solar cell fabrication process system is applied to R2R and R2P according to a second embodiment of the present invention.

Referring FIGS. 14C and D, a real time measurement system S of the CIGS thin film material distribution may be applied to (c) R2R or (d) R2P process, which is continuous process.

The kind of process is different according to the kind of substrate used to CIGS thin film 5 manufactured by the kind of process.

The CIGS thin film 5 applies the real time measurement system (S) of CIGS thin film material distribution to a R2P process using hardened material substrate such as soda-lime.

On the other hand, the CIGS thin film 5 applies the real time measurement system (S) of the CIGS thin film material distribution to R2R process using a metal sheet such as stainless steel, Ti, Mo, Cu and the like and a flexible material substrate of polymer and the like such as polyimide.

A system of the present invention is to provide a process control system for determining whether abnormalities are present or not by measuring a physical and chemical properties on a continuous production process lines of CIGS thin film solar cell in real time, and performing a production and quality management at the same time by providing a feedback on CIGS fabrication process.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A copper indium gallium selenide (CIGS) thin film solar cell fabrication process system comprising:
an object transfer section to continuously transfer a process object for fabrication of CIGS thin film solar cells;
a thin film fabrication process section to perform a CIGS thin film fabrication process on the process object during transfer;
at least one header including at least one laser irradiation sectional to radiate a laser beam to CIGS thin film manufactured by the thin film fabrication process sections, at least one spectroscopy detection optical section to detect the spectroscopy from a plasma generated CIGS thin film by the irradiated laser beam, and a beam irradiation positioning section to adjust an irradiation position of the laser beam;
a header transfer section combined with a transfer path of the object and moving the header in the same speed and direction as a moving speed and a moving direction of the CIGS thin film manufactured by the thin film fabrication process section;
a spectroscopy information storage section in which a spectroscopy state information is stored;
a spectroscopy analyzing section connected electrically to the spectroscopy detection optical section to analyze a material distribution state within the CIGS thin film from the spectroscopy detected by the spectroscopy detection optical section based on the information stored in the spectroscopy information storage section;
a process control section connected to the spectroscopy analyzing section to control the thin film fabrication process section based on the material distribution state within the CIGS thin film analyzed by the spectroscopy analyzing section; and
a scribing section to pattern the CIGS thin film manufactured by the thin film fabrication process section.

2. The CIGS thin film solar cell fabrication process system of claim 1, wherein the laser irradiation section includes a laser section and an auto-focus section.

3. The CIGS thin film solar cell fabrication process system of claim 1, wherein the CIGS thin film fabrication process is CIGS deposition process.

4. The CIGS thin film solar cell fabrication process system of claim 1, wherein the beam irradiation positioning section is a galvanometer.

5. The CIGS thin film solar cell fabrication process system of claim 1, further comprising an index recognition optical section recognizing an index to trace a position that the laser beam is radiated.

6. The CIGS thin film solar cell fabrication process system of claim 1, wherein the scribing comprises a second scribing process.

7. The CIGS thin film solar cell fabrication process system of claim 1, wherein the control modifies a rate and distribution value of an element including CIGS thin film provide a feedback on the thin film fabrication process section.

8. A copper indium gallium selenide (CIGS) thin film solar cell fabrication process system comprising:
an object transfer section to continuously transfer a process object for fabrication of CIGS thin film solar cells;
a thin film fabrication process section to perform a CIGS thin film fabrication process on the process object during transfer;
at least one header including a laser irradiation section for at least one scribing to radiate a laser beam to pattern CIGS thin film manufactured by the thin film fabrication process, at least a spectroscopy detection optical section to detect a spectroscopy from plasma generated from the CIGS thin film by the radiated laser beam, and a beam irradiation positioning section to adjust an irradiation position of the laser beam;

a header transfer section combined with a transfer path of the object and moving the header in the same speed and direction as a moving speed and a moving direction of the CIGS thin film manufactured by the thin film structure process section;

a spectroscopy information storage section in which a spectroscopy state information is stored;

a spectroscopy analyzing section to analyze a material distribution state within the CIGS thin film from the spectroscopy detected by the spectroscopy detection optical section based on the information stored in the spectroscopy information storage section; and a process control section to control the thin film fabrication process section based on the material distribution state within the CIGS thin film analyzed by the spectroscopy analyzing section.

9. The CIGS thin film solar cell fabrication process system of claim 8, wherein the CIGS thin film fabrication process is CIGS deposition process.

10. The CIGS thin film solar cell fabrication process system of claim 8, wherein the beam irradiation positioning section is a galvanometer.

11. The CIGS thin film solar cell fabrication process system of claim 8, further comprising an index recognition optical section recognizing an index to trace a position that the laser beam is radiated.

12. The CIGS thin film solar cell fabrication process system of claim 8, wherein the scribing comprises a second scribing process.

13. The CIGS thin film solar cell fabrication process system of claim 8, wherein the control modifies a rate and distribution value of an element including CIGS thin film provide a feedback on the thin film fabrication process section.

* * * * *